(12) United States Patent
Kim et al.

(10) Patent No.: US 11,944,504 B2
(45) Date of Patent: Apr. 2, 2024

(54) AUTOMATIC TENSION MEASURING INSTRUMENT

(71) Applicant: JSR MEDICAL CO., LTD., Daegu (KR)

(72) Inventors: Jae Hwang Kim, Daegu (KR); Min Ho Jung, Daegu (KR); Chang Young Chae, Gyeongsangbuk-do (KR)

(73) Assignee: JSR MEDICAL CO., LTD., Daegu (KR)

( * ) Notice: Subject to any disclaimer, the term of this patent is extended or adjusted under 35 U.S.C. 154(b) by 1087 days.

(21) Appl. No.: 16/637,224

(22) PCT Filed: Nov. 14, 2017

(86) PCT No.: PCT/KR2017/012838
§ 371 (c)(1),
(2) Date: Feb. 6, 2020

(87) PCT Pub. No.: WO2019/031651
PCT Pub. Date: Feb. 14, 2019

(65) Prior Publication Data
US 2020/0163736 A1 May 28, 2020

(30) Foreign Application Priority Data

Aug. 8, 2017 (KR) ........................ 10-2017-0100427

(51) Int. Cl.
*G01L 5/04* (2006.01)
*A61B 17/12* (2006.01)
(Continued)

(52) U.S. Cl.
CPC ........ *A61B 90/06* (2016.02); *A61B 17/12013* (2013.01); *A61F 5/0066* (2013.01); *G01L 5/04* (2013.01); *A61B 2090/064* (2016.02)

(58) Field of Classification Search
CPC .............. A61B 90/06; A61B 17/12013; A61B 2090/064; A61B 2090/061; A61B 17/12;
(Continued)

(56) References Cited

U.S. PATENT DOCUMENTS 5,449,368 A 9/1995 Kuzmak
5,601,604 A 2/1997 Vincent
(Continued)

FOREIGN PATENT DOCUMENTS

CN 102821637 12/2012
CN 104507399 A 4/2015
(Continued)

OTHER PUBLICATIONS

Extended European Search Report for corresponding European application No. 17920987.9; dated Mar. 11, 2021 (7 pages).
(Continued)

*Primary Examiner* — Freddie Kirkland, III
(74) *Attorney, Agent, or Firm* — TAROLLI, SUNDHEIM, COVELL & TUMMINO L.L.P.

(57) ABSTRACT

The present invention relates to an automatic tension measurer, comprising: a band lengthily formed in a longitudinal direction; a main body formed to allow the band to be guided thereinto such that one-side end portion of the band is fixed and the other-side end portion thereof is drawn to the outside; a marking part implemented in the main body, and formed so as to enable marking in the band at a specific position in response to the tension applied to the band; and a stopper formed in the main body, and stopping the band at a specific position.

16 Claims, 9 Drawing Sheets

(51) Int. Cl.
*A61B 90/00* (2016.01)
*A61F 5/00* (2006.01)

(58) Field of Classification Search
CPC . A61B 2017/00818; A61B 2017/12018; A61F 5/0066; A61F 2/04; A61F 5/005; A61F 2002/045; G01L 5/04
See application file for complete search history.

(56) References Cited

U.S. PATENT DOCUMENTS

| | | | | |
|---|---|---|---|---|
| 6,676,674 | B1 * | 1/2004 | Dudai | A61F 5/0066 |
| | | | | 606/151 |
| 8,900,117 | B2 * | 12/2014 | Birk | A61F 5/0066 |
| | | | | 606/151 |
| 8,920,307 | B2 * | 12/2014 | Marcotte | A61F 5/005 |
| | | | | 600/37 |
| 9,339,272 | B2 | 5/2016 | Khosrovaninejad | |
| 9,795,391 | B2 * | 10/2017 | Saatchi | A61B 17/135 |
| 11,369,383 | B2 * | 6/2022 | Kim | A61B 17/1114 |
| 11,564,695 | B2 * | 1/2023 | Dahl | A61B 50/33 |
| 2004/0153106 | A1 | 8/2004 | Dudai | |
| 2008/0312682 | A1 * | 12/2008 | Shams | A61B 17/1327 |
| | | | | 606/203 |
| 2013/0144311 | A1 * | 6/2013 | Fung | A61B 17/12013 |
| | | | | 606/139 |
| 2015/0157327 | A1 * | 6/2015 | Hoglund | A61B 17/12009 |
| | | | | 606/158 |
| 2016/0198783 | A1 | 7/2016 | Ryou | |
| 2021/0113213 | A1 * | 4/2021 | Dahl | A61F 5/32 |

FOREIGN PATENT DOCUMENTS

| | | |
|---|---|---|
| EP | 1036545 A2 | 9/2000 |
| EP | 1036545 A3 | 3/2001 |
| KR | 20110129889 A | 12/2011 |
| KR | 101649351 B1 | 8/2016 |
| KR | 20170021617 A | 2/2017 |
| KR | 101721337 B1 | 3/2017 |
| WO | 2012170652 A1 | 12/2012 |
| WO | 2014007719 A1 | 1/2014 |
| WO | 2014038736 A1 | 3/2014 |

OTHER PUBLICATIONS

International Search Report for corresponding International application No. PCT/KR2017/012838; dated Apr. 13, 2018 (2 pages).
Office Action issued for corresponding CN110996832 dated Sep. 9, 2022.

* cited by examiner

AUTOMATIC TENSION MEASURING INSTRUMENT

TECHNICAL FIELD

The present invention relates to an automatic tension measuring instrument, and more particularly to an automatic tension measuring instrument capable of performing marking at a specific position of a band in response to tension applied to the band, whereby it is possible to easily estimate an ideal length of an intestinal band.

BACKGROUND ART

Colon cancer is a malignant tumor generated in the colon and the rectum, and most of colon cancer is adenocarcinoma generated in mucous membranes of the large intestine. In addition to adenocarcinoma, squamous cell carcinoma, malignant lymphoma, malignant sarcoma, and malignant carcinoid tumor are found on rare occasions. Once in a while, cancers generated in internal organs around the large intestine invade the large intestine, or cancers generated in regions other than the internal organs spread to the large intestine. Most of adenocarcinoma is generated as the result of growth of a benign tumor (polyp), which is an adenoma.

Colon cancer may be classified into ascending colon cancer, descending colon cancer, and rectal cancer based on the position of a lesion. Descending colon cancer has a higher disease incidence rate than ascending colon cancer, and rectal cancer has a higher disease incidence rate than descending colon cancer. The reason for this is that the effect of a pancreatic enzyme gradually decreases downwards.

In general, surgical operation of colon cancer includes incising the upper and lower ends of a diseased region and connecting normal regions to each other by stitching. However, anastomotic leakage after surgical operation may cause a serious postoperative complication, and may threaten the life of a patient. In addition, anastomotic stricture occurs for the long run, whereby the quality of life of the patient is seriously deteriorated.

It is reported that the frequency of occurrence of anastomotic leakage after surgical operation of colon cancer is about 8% to 25%, which is very high. In addition, since, for rectal cancer, which has the highest disease incidence rate, even the region adjacent to the anus is removed although the anus is not removed, normal bowel movement is attended with a serious difficulty even through a convalescent stage after surgical operation, unlike colon cancer patients, who are capable of performing normal bowel movement through a convalescent stage after surgical operation.

For temporary stoma (abdominal stoma) generally formed in order to reduce damage due to such anastomotic leakage, bowel movement based on the peristaltic movement of a large intestine is impossible, whereby feces are discharged at all times. Consequently, a colostomy bag must be worn at all times. As a result, limitations in activity and bad smells due to leaking feces may become an issue.

Management of such stoma is very troublesome and inconvenient. Above all, many patients feel severe mental pains for various reasons, such as bad smells due to leaking feces, biased views of people around the patients, limitations in activity, and inconvenience in wearing normal clothes, whereby the quality of life of the patients is deteriorated.

In order to solve such a problem, an artificial intestinal tract system for bypass of feces has been proposed in recent years.

A conventional artificial intestinal tract system includes an intestinal tract tube and a pair of fixing tubes. The artificial intestinal tract system is inserted into an intestinal tract, and the portion of the artificial intestinal tract system between the fixing tubes is fixed to the intestinal tract outside the intestinal tract using an intestinal tract band.

The most important thing in using the artificial intestinal tract system is to stably fix the artificial intestinal tract system to the intestinal tract, to prevent necrosis of the intestinal tract due to fixation, and to easily remove the artificial intestinal tract system after a predetermined period of time.

To this end, research on a biodegradable band has been actively conducted.

The biodegradable band is coupled to the portion of the artificial intestinal tract system between the fixing tubes. Since the biodegradable band must stably fix the artificial intestinal tract system, deformation or loosening of the biodegradable band must be minimized even though peristaltic movement is performed, and necrosis of the intestinal tract due to fixation must be prevented, it is very important supply the biodegradable band so as to exhibit appropriate tension while having a predetermined length.

Installation of a conventional biodegradable band is achieved by manually surrounding a biodegradable band estimated to have an appropriate length on the circumference of the intestinal tract between the fixing tubes and performing stitching or using a band installer capable of performing stitching and cutting at a predetermined length.

In the case in which the above method is used, however, it is not easy to supply a band having a length suitable for a patient, i.e. appropriate tension, and it is not easy to rapidly supply a band suitable for a patient at the time of surgical operation.

DISCLOSURE

Technical Problem

The present invention has been made in view of the above problems, and it is an object of the present invention to provide an automatic tension measuring instrument capable of performing marking at a specific position of a band in response to tension applied to the band, whereby it is possible to easily estimate an ideal length of an intestinal band.

Technical Solution

In accordance with the present invention, the above and other objects can be accomplished by the provision of an automatic tension measuring instrument including a band formed long in a longitudinal direction, a main body formed to allow the band to be guided thereinto such that one end of the band is fixed and the other end of the band is drawn outside, a marking part provided in the main body, the marking part being formed so as to enable marking on the band at a specific position in response to tension applied to the band, and a stopper formed at the main body, the stopper being configured to stop the band at a predetermined position.

In addition, the main body may be provided with a first guideway, to which the one end of the band is coupled and along which the one end of the band is guided, and a second guideway, to which the other end of the band is coupled and along which the other end of the band is guided so as to be drawn outside the main body.

In addition, a band fixing part configured to fix the one end of the band to one side of the main body may be formed at one side of the first guideway, and a window part formed so as to communicate with the second guideway and configured to expose a specific portion of the band outside may be provided.

In addition, a marking part may be provided in a predetermined region of the window part in order to mark a specific position of the exposed band, and the marking may be performed by elastically pushing the specific position of the exposed band.

In addition, a receiving part formed so as to communicate with the second guideway and configured to provide a gap in which the stopper is operated may be formed, and the stopper may include a pushing part coupled to the receiving part, an elastic plate coupled to the pushing part in the state in which one side thereof is fixed to the main body, the other side of the elastic plate being elastically operated in a vertical direction by operation of the pushing part, and a fixing protrusion formed at the other side of the elastic plate in order to fix the position of the band or to release the fixed position of the band by the elastic vertical operation of the elastic plate.

In addition, the fixing protrusion may be formed so as to fix the position of the band in the state in which the band is drawn outside in a direction toward one side of the main body and to have a smaller inclination in an advancing direction of the band such that the band is not moved in the opposite direction.

Meanwhile, a cutting recess formed in the direction toward the one side of the main body so as to be adjacent to the marking part and configured to communicate with the first guideway and the second guideway in order to expose the band outside such that the band can be cut may be provided.

Here, the band may be any one of an intestinal band, an auxiliary band, and an intestinal band/auxiliary band.

In addition, the band may be formed long in the longitudinal direction and may be provided at the other end thereof with a cutting prearrangement part configured to be cut when pulled at predetermined tension, the band may be provided with a plurality of catching holes formed in the longitudinal direction so as to catch the stopper such that the position of the band is fixed by the stopper, and an indication part may be formed at a specific position of the band.

In addition, the automatic tension measuring instrument may be configured to measure tension applied to the band such that the stopper is operated when the tension reaches a predetermined level and marking is enabled on the band at that position.

Meanwhile, in the automatic tension measuring instrument, the distance from the portion marked on the band by the marking part to the portion of the band abutting fixing tubes of an artificial intestinal tract system may be 5 mm to 15 mm in response to the tension applied to the band.

Advantageous Effects

The present invention has the effect of providing an automatic tension measuring instrument capable of estimating an ideal length of an intestinal band configured to fix an artificial intestinal tract system, wherein marking is performed at a specific position of a band in response to tension applied to an intestinal band, an auxiliary band, and an intestinal band/auxiliary band, whereby it is possible to easily estimate an ideal length of the intestinal band.

In particular, the present invention has the effect that one end of the band is fixed, the band is located on the portion of an artificial intestinal tract system between fixing tubes, a specific position of the band is marked when predetermined tension is applied to the band while the other end of the band is moved, whereby it is possible to estimate the length of the intestinal band most suitable for a patient and thus to achieve rapid application of a user-customized intestinal band.

BEST MODE

The present invention relates to an automatic tension measuring instrument capable of estimating an ideal length of an intestinal band configured to fix an artificial intestinal tract system, wherein marking is performed at a specific position of a band in response to tension applied to an intestinal band, an auxiliary band, and an intestinal band/ auxiliary band, whereby it is possible to easily estimate an ideal length of the intestinal band.

In particular, one end of the band is fixed, the band is located on the portion of an artificial intestinal tract system between fixing tubes, a specific position of the band is marked when predetermined tension is applied to the band while the other end of the band is moved, whereby it is possible to estimate the length of the intestinal band most suitable for a patient and thus to achieve rapid application of a user-customized intestinal band.

Hereinafter, an embodiment of the present invention will be described in detail with reference to the accompanying drawings.

Figure 1:
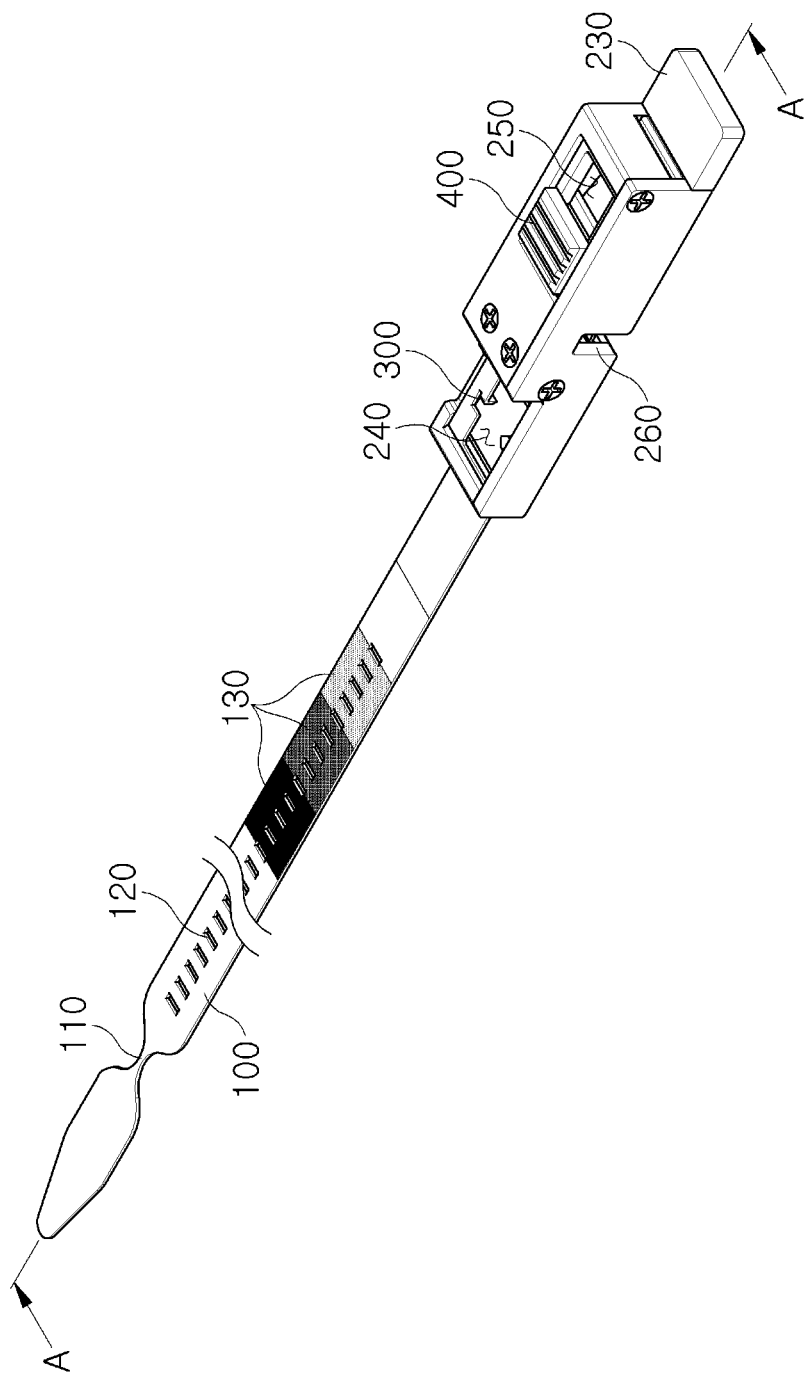
FIG. 1 is a perspective view according to an embodiment of the present invention.
Figure 2:
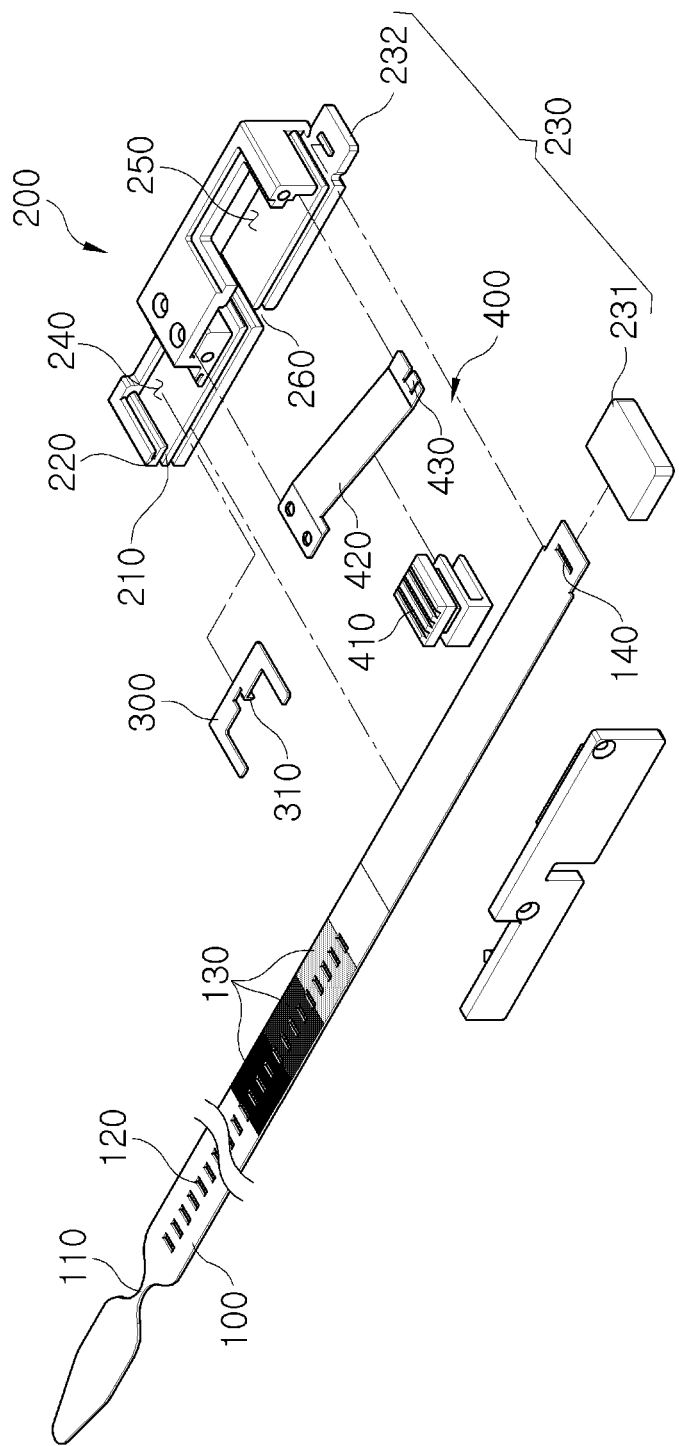
FIG. 2 is an exploded perspective view according to an embodiment of the present invention.
Figure 3:
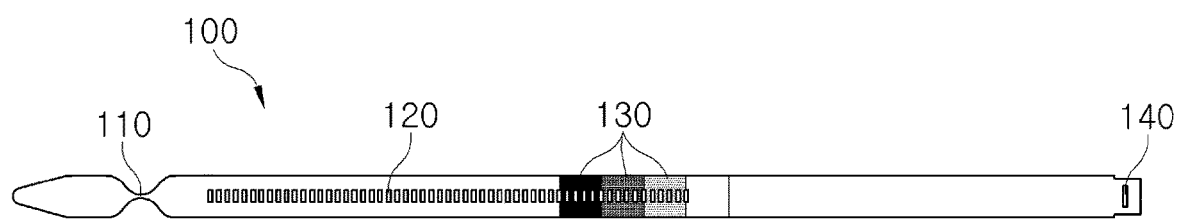
FIG. 3 is a front view of an auxiliary band according to an embodiment of the present invention.
Figure 4:
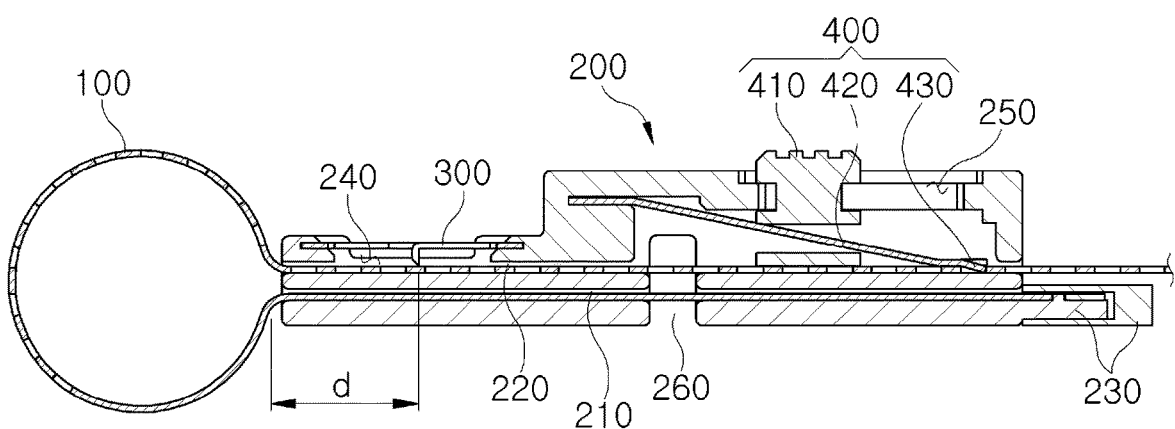
FIG. 4 is a sectional view according to an embodiment of the present invention.
Figure 5A:
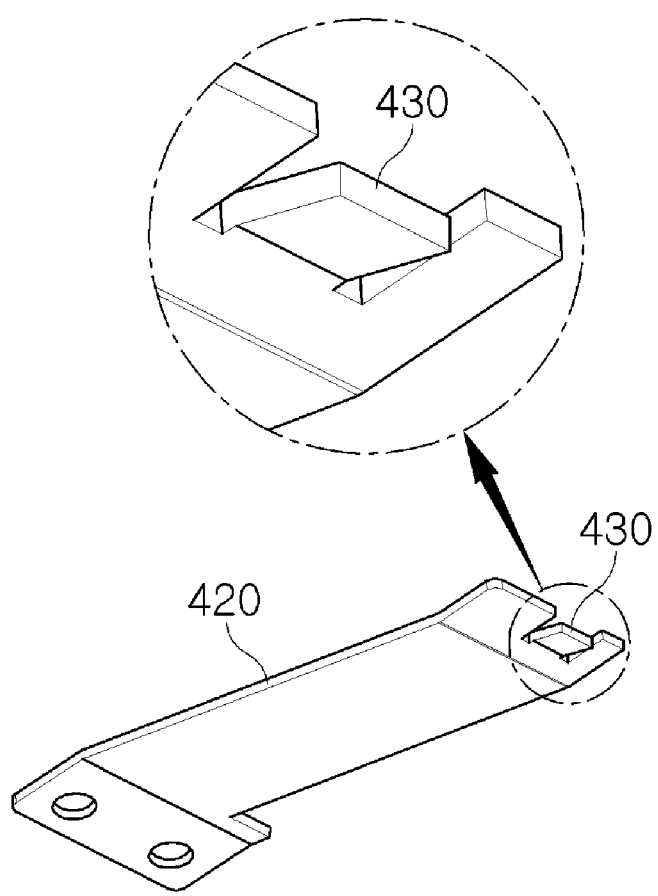
FIGS. 5A and 5B are views showing an embodiment of a fixing protrusion of a stopper of the present invention.
Figure 5B:
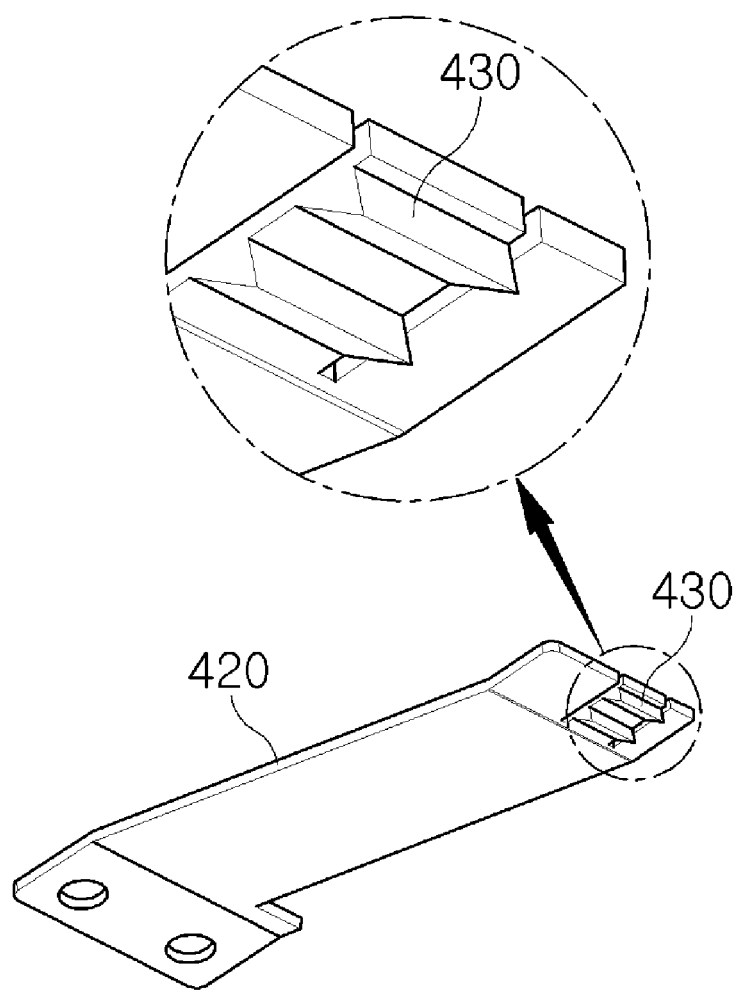

FIG. 1 is a perspective view according to an embodiment of the present invention, FIG. 2 is an exploded perspective view according to an embodiment of the present invention, FIG. 3 is a front view of an auxiliary band according to an embodiment of the present invention, FIG. 4 is a sectional view according to an embodiment of the present invention, FIGS. 5A and 5B are views showing an embodiment of a fixing protrusion of a stopper of the present invention, and FIG. 6 is an illustrative view of operation according to an embodiment of the present invention.

As shown, an automatic tension measuring instrument according to the present invention is characterized by including a band 100, a main body 200 formed to allow the band 100 to be guided thereinto such that one end of the band 100 is fixed and the other end of the band is drawn outside, a marking part 300 provided in the main body 200, the marking part being formed so as to enable marking on the band 100 at a specific position in response to tension applied to the band 100, and a stopper 400 formed at the main body 200, the stopper 400 being configured to stop the band 100 at a predetermined position.

That is, the band 100 is coupled to the interior of the automatic tension measuring instrument, surrounds the portion of an artificial intestinal tract system 10 between fixing tubes 11, a specific position of the band 100 is marked when predetermined tensile force is applied to the band 100, and the position of the band is fixed, whereby it is possible to estimate an ideal length of an intestinal band.

First, the band 100 according to the present invention is formed long in a longitudinal direction, and is formed as any one of a biodegradable intestinal band configured to fix a well-known artificial intestinal tract system 10, an auxiliary band, and an intestinal band/auxiliary band formed by overlapping the biodegradable intestinal band and the auxiliary band each other. In the case in which the intestinal band and the auxiliary band are used together, the auxiliary band is located at the inside, i.e. the portion abutting the intestinal tract.

In general, the intestinal band is woven using yarn, is configured not to be untied when fixing the artificial intestinal tract system 10, is configured to exhibit tensile strength to some extent and not to be deformed even by peristaltic movement of the large intestine, and is made of a material that is biodegradable after a predetermined period of time while not damaging the outer wall of the large intestine. The intestinal band is generally woven using a mesh-shaped biodegradable stitching fiber and is then provided.

The auxiliary band 100 is made of a polymer material, such as polyurethane, and is made of a slippery and transparent material.

Each of the intestinal band and the auxiliary band is made of a material configured to extend when tension is applied thereto and to be automatically cut when the tension reaches a predetermined level or more or a material configured to be automatically cut when the tension reaches a predetermined level or more.

Hereinafter, the case in which the auxiliary band is used as an embodiment of the present invention will be described as an important point.

As shown in FIG. 3, the case in which a cutting prearrangement part 110 configured to be cut when pulled at predetermined tension is formed at the other end of the auxiliary band 100 is shown. The cutting prearrangement part is provided so as to be cut when pulled at a force of about 1 kg to 1.5 kg, and is designed such that the length of the auxiliary band 100 when surrounding the portion of the artificial intestinal tract system 10 between the fixing tubes 11 and cut at predetermined tension is estimated to be an ideal length of the intestinal band.

In addition, the auxiliary band 100 may be designed such that tension applied to the auxiliary band is measured, the stopper is operated when the tension reaches a predetermined level, and marking is enabled on the auxiliary band 100 at that position, whereby the ideal length of the intestinal band is estimated based thereon. That is, a pressure sensor is installed in order to measure tension, i.e. pressure, applied to the auxiliary band 100, a predetermined pressure level is set, and the stopper is automatically operated when the pressure reaches the predetermined pressure level, whereby it is possible to automatically measure tension.

Meanwhile, the intestinal band may be directly used in place of the auxiliary band, or a combination of the intestinal band/the auxiliary band may also be used. In the case in which the combination of the intestinal band/the auxiliary band is used, the intestinal band and the auxiliary band may be partially fixed to each other using a fixing hanger such that the intestinal band and the auxiliary band are prevented from moving separately.

In addition, the auxiliary band 100 is provided with a plurality of catching holes 120 formed in the longitudinal direction so as to catch the stopper 400 such that the position of the auxiliary band 100 is fixed by the stopper 400, and a scale for size estimation may be marked on the entirety of the auxiliary band 100 or an indication part 130 may be formed at a specific position at which an effective region that can be estimated as an ideal length is marked in advance, as shown in FIG. 3.

The main body 200 is formed such that the auxiliary band 100 is guided thereinto, one end of the auxiliary band 100 is fixed, and the other end of the auxiliary band is drawn outside, and has a structure in which the auxiliary band 100 is coupled to the interior thereof and the marking part 300, and the stopper 400, a description of which will follow, are provided at one side thereof.

As an embodiment of the present invention, the main body 200 is provided with a first guideway 210, to which one end of the auxiliary band 100 is coupled and along which the one end of the auxiliary band is guided, and a second guideway 220, to which the other end of the auxiliary band 100 is coupled and along which the other end of the auxiliary band is guided so as to be drawn outside the main body 200.

A band fixing part 230 configured to fix one end of the auxiliary band 100 to one side of the main body 200 is formed at one side of the first guideway 210, and, when the one end of the auxiliary band 100 is coupled, guided, and is drawn to one side of the main body 200 via the first guideway 210, the one end of the auxiliary band 100 is fixed by the band fixing part 230 formed at the one side of the main body 200.

The band fixing part 230 is configured to fix one end of the auxiliary band 100 to one side of the main body 200, and holds the one end of the auxiliary band 100 in the form of clamps or is formed as male and female band fixing parts 230, as shown, such that, when a catching recess 140 is formed in the auxiliary band 100 and a male band fixing part 232 is caught in the catching recess, a female band fixing part 231 is coupled to the male band fixing part, whereby the one end of the auxiliary band 100 is securely fixed to the one side of the main body 200.

The second guideway 220 is formed so as to be open at the front and rear thereof such that the auxiliary band 100 is inserted and coupled, passes through the interior of the main body 200, and is drawn outside the main body 200, and, when the other end of the auxiliary band 100 that has passed through the second guideway 220 is drawn outside the main body 200 in the state in which one end of the auxiliary band 100 is fixed by the band fixing part 230, predetermined tension is applied thereto, whereby the other end of the auxiliary band 100 is pulled.

As a result, the cutting prearrangement part 110 formed at the other end of the auxiliary band 100 is cut, and the pulled position of the auxiliary band 100 is marked, whereby it is possible to estimate an ideal length of the intestinal band.

In addition, a window part 240 formed so as to communicate with the second guideway 220 and configured to expose a specific portion of the auxiliary band 100 outside is provided in the main body 200.

The window part 240 is configured to enable a user to observe the form in which the auxiliary band 100 moves as the other end of the auxiliary band 100 is pulled, whereby it is possible to recognize the indication part 130 of the auxiliary band 100 outside.

The marking part 300 is provided in the main body 200, and is formed such that marking is enabled on the auxiliary band 100 at a specific position.

Specifically, the marking part 300 is provided in a predetermined region of the window part 240 in order to mark a specific position of the exposed auxiliary band 100.

That is, when the cutting prearrangement part 110 is cut as the auxiliary band 100 is pulled at predetermined tension, marking is performed on the portion of the auxiliary band 100 exposed through the window part 240.

The marking on the auxiliary band 100 may be performed through a writing utensil, or, as an embodiment of the present invention, the marking part 300 may be provided using a method of elastically pushing a specific position of the exposed auxiliary band 100.

The marking part 300 is provided in a predetermined region of the window part 240, and, as an embodiment, is made of a metal plate as a whole, and is fixed to opposite sides of the window part 240 so as to cover the window part 240. A concave-convex pin 310 for marking on the auxiliary band 100 is provided at a specific position of the marking part 300, and pushes the marking part 300 at a specific position of the auxiliary band 100 passing through the second guideway 220, whereby marking is performed on the auxiliary band 100 by the concave-convex pin 310.

The marking part 300 is formed such that elastic force is applied upwards and downwards by a thin metal plate and so as to return to the original position thereof after marking is performed at a specific position of the auxiliary band 100.

The stopper 400 is formed at the main body 200 in order to stop the auxiliary band 100 at a predetermined position. Specifically, the stopper 400 is coupled to a receiving part 250 formed so as to communicate with the second guideway 220 and configured to provide a gap in which the stopper 400 is operated, and, when marking is completed by the marking part 300, serves to fix the auxiliary band 100 at that position.

The stopper 400 includes a pushing part 410 coupled to the receiving part 250, an elastic plate 420 coupled to the pushing part 410 in the state in which one side thereof is fixed to the main body 200, the other side of the elastic plate being elastically operated in a vertical direction by the operation of the pushing part 410, and a fixing protrusion 430 formed at the other side of the elastic plate 420 in order to fix the position of the auxiliary band 100 or to release the fixed position of the auxiliary band by the elastic vertical operation of the elastic plate 420.

The pushing part 410 is exposed so as to be exposed outside the receiving part 250, and, when the user operates the pushing part 410, the elastic plate 420 is moved upwards and downwards. Since the elastic plate 420 is moved in the state in which one side thereof is fixed to the main body 200, only the other side of the elastic plate 420 is elastically operated in the vertical direction by the operation of the pushing part 410. The fixing protrusion 430 is formed at the other side of the elastic plate 420 in order to fix the position of the auxiliary band 100 or to release the fixed position of the auxiliary band by the elastic vertical operation of the elastic plate 420.

That is, in the case in which the auxiliary band 100 is to be moved freely, the pushing part 410 is pushed to one side of the main body 200 (FIG. 6A) to move the other side of the elastic plate 420 upwards, and, in the case in which the auxiliary band 100 is to be fixed or the auxiliary band 100 is to be moved in the state in which the stopper 400 (the fixing protrusion 430) is caught in one of the catching holes 120 of the auxiliary band 100, the pushing part 410 is pushed to the other side of the main body 200 (FIG. 6B) to move the other side of the elastic plate 420 downwards.

The fixing protrusion 430 formed at the other side of the elastic plate 420 is formed so as to fix the position of the auxiliary band 100 in the state in which the auxiliary band 100 is drawn outside in a direction toward one side of the main body 200 and to have a smaller inclination in the advancing direction of the auxiliary band 100 such that the auxiliary band 100 is not moved in the opposite direction.

FIGS. 5A and 5B are bottom perspective views showing an elastic plate 420 according to an embodiment of the present invention. A fixing protrusion 430 according to an embodiment of the present invention is formed at the other side of the elastic plate 420, is formed so as to protrude downwards in a plate shape (FIG. 5A) or in a protrusion shape (FIG. 5B), is formed so as to be caught in one of the catching holes 120 of the auxiliary band 100, is formed so as to have a smaller inclination in the advancing direction of the auxiliary band 100 such that the auxiliary band 100 can be moved to one side (in a direction toward one side of the main body 200) and cannot be moved in the opposite direction (one-way stopper).

Meanwhile, a cutting recess 260 is further formed in a direction toward one side of the main body 200 so as to be adjacent to the marking part 300, and communicates with the first guideway 210 and the second guideway 220 to expose the auxiliary band 100 outside such that the auxiliary band 100 can be cut.

When the cutting prearrangement part 110 of the auxiliary band 100 is cut and marking is completed at a specific position of the auxiliary band 100 (FIG. 6C), as described above, the auxiliary band 100 is cut through the cutting recess 260, and the entire auxiliary band 100 is drawn from the main body 200, whereby it is possible to estimate the length from the marked portion (a first reference) to the position at which the auxiliary band is inserted in to the first guideway 210 (a second reference) as an ideal length of the intestinal band.

The length from the marked portion, i.e. the first reference, to the second reference may be adjusted depending on the length or shape of the main body 200, and the length of the intestinal band provided by the automatic tension measuring instrument according to the present invention so as to guarantee effective tensile force to the intestinal band and to stitch and fix the intestinal band while not disturbing peristalsis is estimated so as to have a small allowance.

Here, in the automatic tension measuring instrument, the distance d from the portion marked on the auxiliary band 100 by the marking part 300 to the portion of the auxiliary band 100 abutting the fixing tubes 11 of the artificial intestinal tract system 10 is preferably 5 mm to 15 mm in response to the tension applied to the auxiliary band 100.

This configuration is set to provide a small allowance to the length of the intestinal band, and is connected with tension at which the auxiliary band 100 is cut when pulled (for example, 1 to 2 kg). For example, in the case in which the length of the intestinal band is about 10 mm when the intestinal band is pulled at a tension of 1 kg, the length of the intestinal band is about 13 mm when the intestinal band is pulled at a tension of 1.5 kg.

Figure 6A:
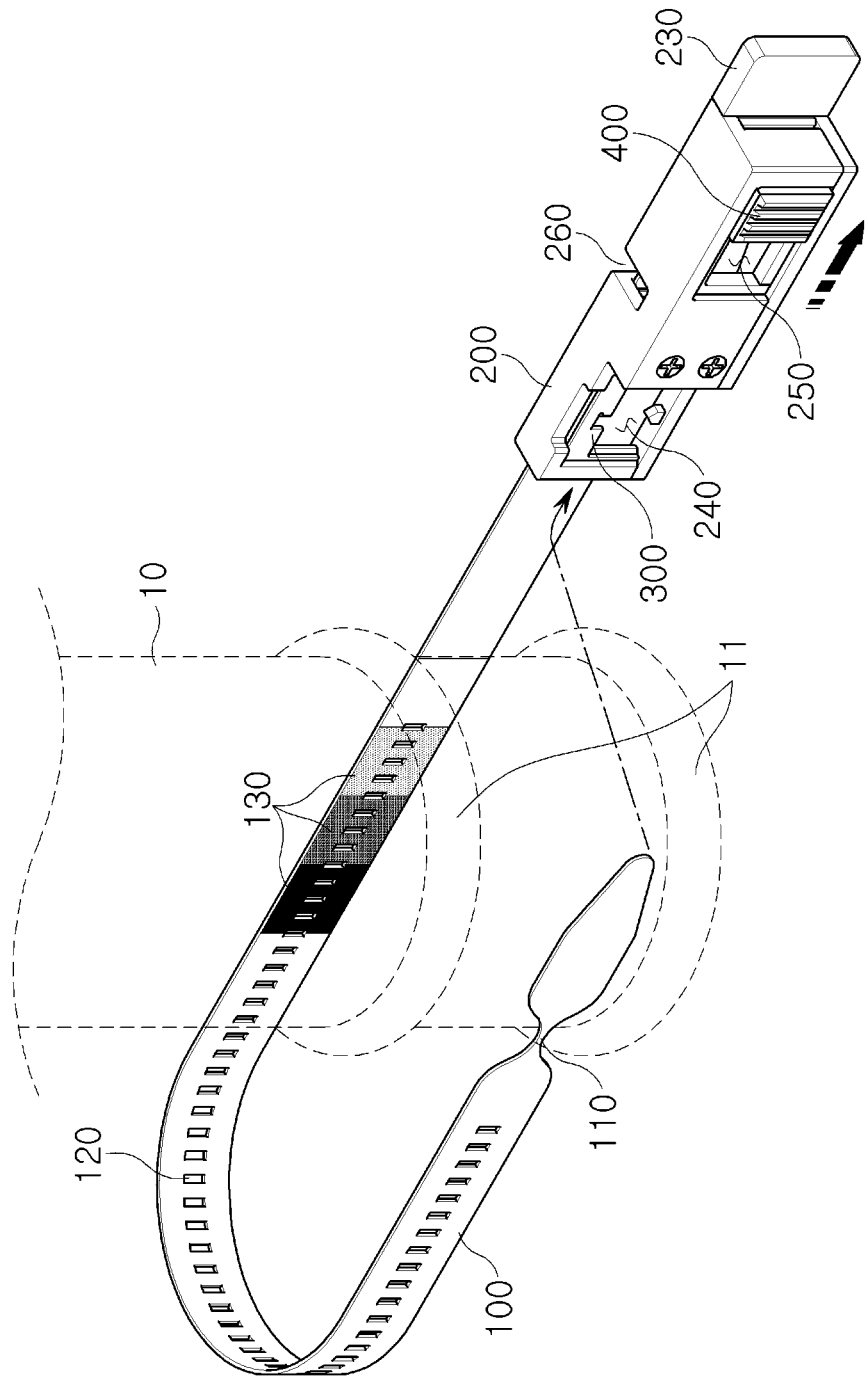
FIGS. 6A, 6B, 6C, and 6D are illustrative views of operation according to an embodiment of the present invention.
Figure 6B:
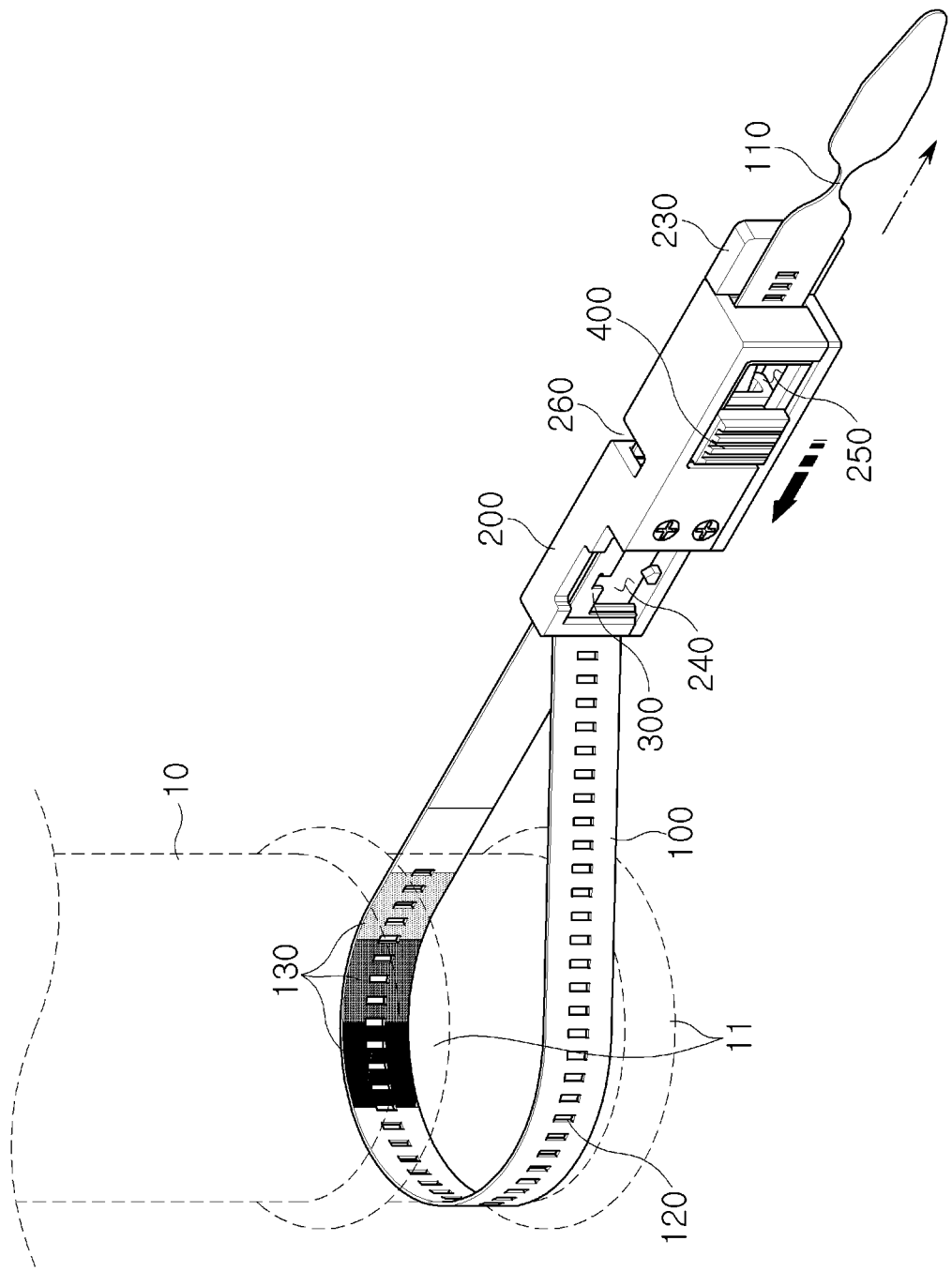
Figure 6C:
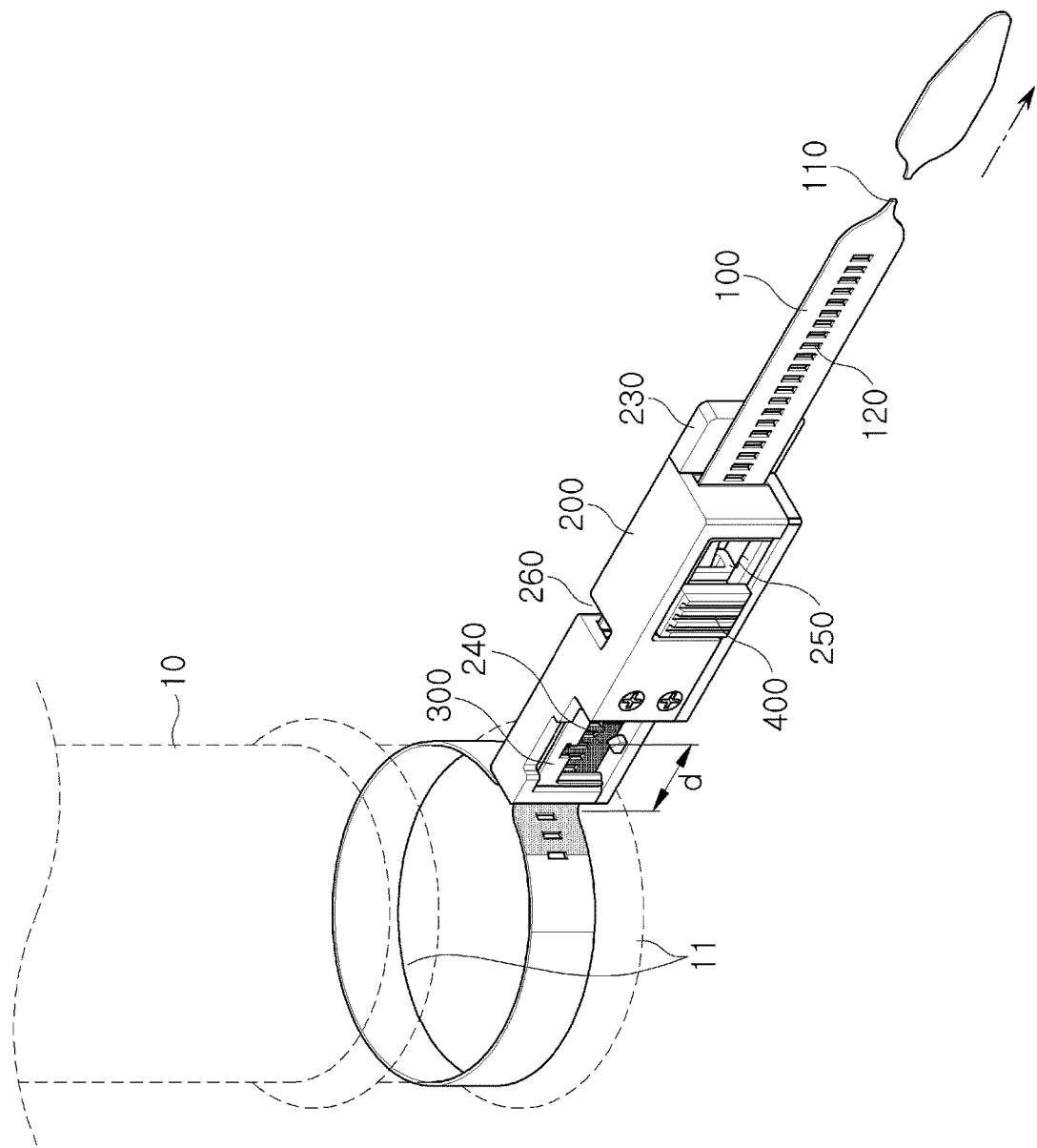
Figure 6D:
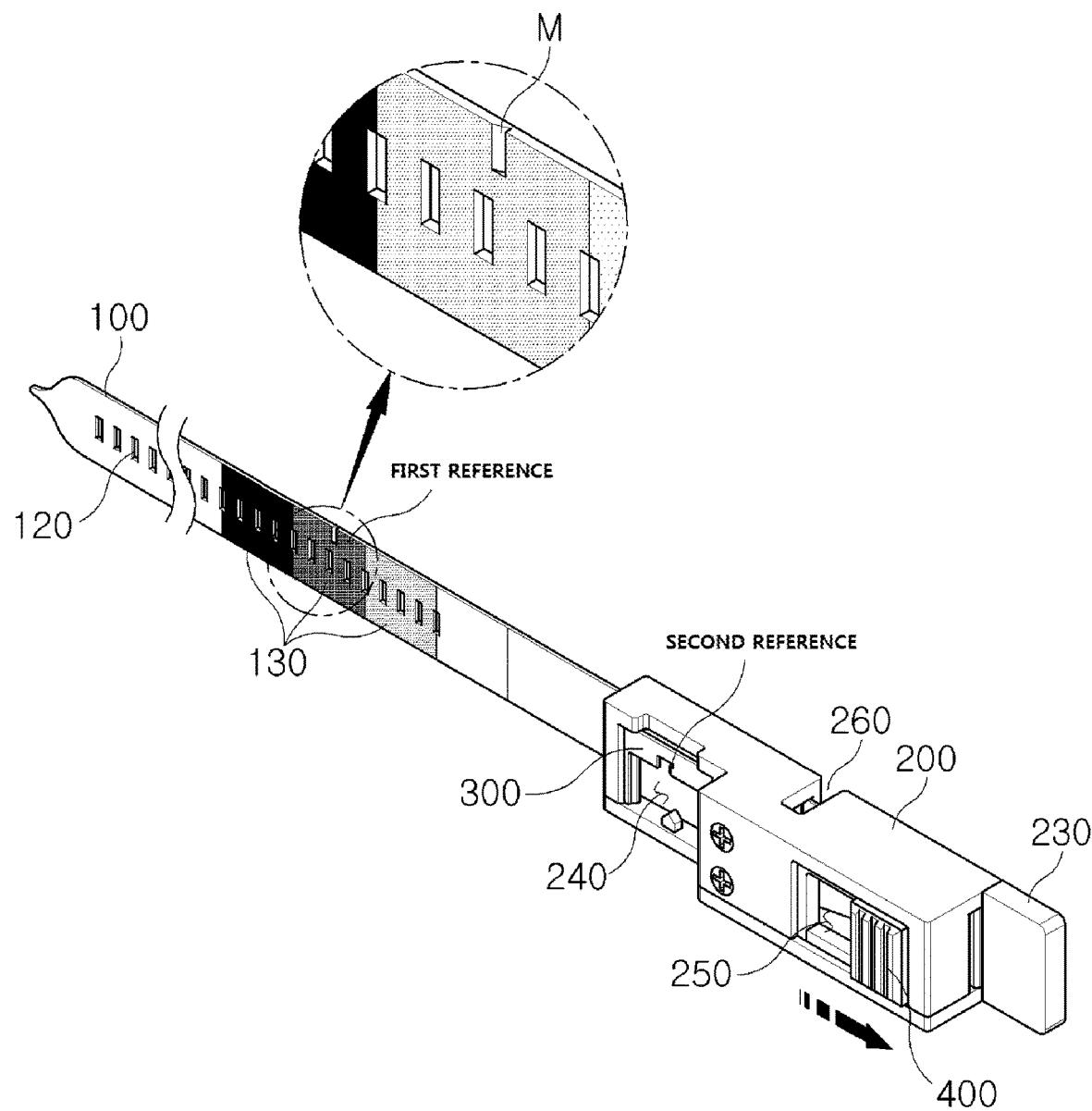

In addition, when the cutting prearrangement part 110 of the auxiliary band 100 is cut and marking is completed at a specific position of the auxiliary band 100 (FIG. 6C), the auxiliary band 100 may not be drawn through the cutting recess 260, but the stopper 400 may be moved in a direction toward one side of the main body 200 in order to raise the elastic plate 420, to release coupling between the fixing protrusion 430 and one of the catching holes 120 of the auxiliary band 100, and to draw the auxiliary band 100 through the second guideway 220 in a direction toward the other side of the main body 200 (FIG. 6D). In this state, a marking M is formed on the auxiliary band 100.

As described above, it is possible to estimate the length from the marked portion(M), i.e. the first reference, to the set second reference as an ideal length of the intestinal band.

Hereinafter, an illustration of operation according to an embodiment of the present invention shown in FIG. 6 will be described.

As shown in FIG. 6A, one end of the auxiliary band 100 is guided through the first guideway 210 of the main body 200 and is fixed by the band fixing part 230 at one side of the main body 200, and the other end of the auxiliary band 100 is placed so as to surround the portion of the artificial intestinal tract system 10 between the fixing tubes 11, is guided through the second guideway 220 of the main body 200, and is drawn to the one side of the main body 200.

At this time, the stopper 400 is pushed in a direction toward one side of the main body 200 to raise the elastic plate 420, whereby coupling between the fixing protrusion 430 and one of the catching holes 120 is released, and therefore the auxiliary band 100 is moved freely.

As shown in FIG. 6B, as the auxiliary band 100 is moved to some extent, the stopper 400 is pushed in a direction toward the other side of the main body 200 to raise the elastic plate 420, whereby coupling between the fixing protrusion 430 and one of the catching holes 120 is performed, and therefore the position of the auxiliary band 100 is fixed carefully as tension is increasingly applied to the auxiliary band.

As shown in FIG. 6C, when the cutting prearrangement part of the auxiliary band 100 is cut at tension appropriate to fix the fixing tubes 11 of the artificial intestinal tract system 10 to the intestinal tract, the marking part 300 is operated to perform marking at a specific position of the auxiliary band 100. In this state, the auxiliary band 100 is fixed so as to be prevented from being moved in the opposite direction (a direction toward the other side of the main body 200) by the stopper 400.

As shown in FIG. 6D, the stopper 400 is moved to a direction toward one side of the main body 200 in order to raise the elastic plate 420, to release coupling between the fixing protrusion 430 and one of the catching holes 120, to draw the auxiliary band 100 in a direction toward the other side of the main body 200 through the second guideway 220, and to measure the length from the marked portion M (the first reference) to the second reference, whereby an ideal length of the intestinal band is estimated.

As is apparent from the above description, the present invention provides an automatic tension measuring instrument capable of estimating an ideal length of an intestinal band configured to fix an artificial intestinal tract system, wherein marking is performed at a specific position of a band in response to tension applied to an intestinal band, an auxiliary band, and an intestinal band/auxiliary band, whereby it is possible to easily estimate an ideal length of the intestinal band.

In particular, one end of the band is fixed, the band is located on the portion of an artificial intestinal tract system between fixing tubes, a specific position of the band is marked when predetermined tension is applied to the band while the other end of the band is moved, whereby it is possible to estimate the length of the intestinal band most suitable for a patient and thus to achieve rapid application of a user-customized intestinal band.

The invention claimed is:

1. An automatic tension measuring instrument comprising:
   a band formed long in a longitudinal direction;
   a main body formed to allow the band to be guided thereinto such that one end of the band is fixed and the other end of the band is drawn outside;
   a marking part provided in the main body, the marking part being formed so as to enable marking on the band at a specific position in response to tension applied to the band; and
   a stopper formed at the main body, the stopper being configured to stop the band at a predetermined position.

2. The automatic tension measuring instrument according to claim 1, wherein the main body is provided with:
   a first guideway, to which the one end of the band is coupled and along which the one end of the band is guided; and
   a second guideway, to which the other end of the band is coupled and along which the other end of the band is guided so as to be drawn outside the main body.

3. The automatic tension measuring instrument according to claim 2, wherein a band fixing part configured to fix the one end of the band to one side of the main body is formed at one side of the first guideway.

4. The automatic tension measuring instrument according to claim 2, wherein a window part formed so as to communicate with the second guideway and configured to expose a specific portion of the band outside is provided.

5. The automatic tension measuring instrument according to claim 4, wherein a marking part is provided in a predetermined region of the window part in order to mark a specific position of the exposed band.

6. The automatic tension measuring instrument according to claim 5, wherein the marking is performed by elastically pushing the specific position of the exposed band.

7. The automatic tension measuring instrument according to claim 2, wherein a receiving part formed so as to communicate with the second guideway and configured to provide a gap in which the stopper is operated is formed.

8. The automatic tension measuring instrument according to claim 7, wherein the stopper comprises:
   a pushing part coupled to the receiving part;
   an elastic plate coupled to the pushing part in a state in which one side thereof is fixed to the main body, the other side of the elastic plate being elastically operated in a vertical direction by operation of the pushing part; and
   a fixing protrusion formed at the other side of the elastic plate in order to fix a position of the band or to release the fixed position of the band by the elastic vertical operation of the elastic plate.

9. The automatic tension measuring instrument according to claim 8, wherein the fixing protrusion is formed so as to fix the position of the band in a state in which the band is drawn outside in a direction toward one side of the main body and to have a smaller inclination in an advancing direction of the band such that the band is not moved in an opposite direction.

10. The automatic tension measuring instrument according to claim 2, wherein a cutting recess formed in a direction toward one side of the main body so as to be adjacent to the marking part and configured to communicate with the first guideway and the second guideway in order to expose the band outside such that the band can be cut is provided.

11. The automatic tension measuring instrument according to claim 1, wherein the band is any one of an intestinal band, an auxiliary band, and an intestinal band/auxiliary band.

12. The automatic tension measuring instrument according to claim 1, wherein the band is provided at the other end thereof with a cutting prearrangement part configured to be cut when pulled at predetermined tension.

13. The automatic tension measuring instrument according to claim 1, wherein the automatic tension measuring instrument is configured to measure tension applied to the band such that the stopper is operated when the tension reaches a predetermined level and marking is enabled on the band at that position.

14. The automatic tension measuring instrument according to claim 1, wherein the band is provided with a plurality of catching holes formed in the longitudinal direction so as to catch the stopper such that the position of the band is fixed by the stopper.

15. The automatic tension measuring instrument according to claim 1, wherein an indication part is formed at a specific position of the band.

16. The automatic tension measuring instrument according to claim 1, wherein a distance (d) from a portion marked on the band by the marking part to a portion of the band abutting fixing tubes of an artificial intestinal tract system is 5 mm to 15 mm in response to the tension applied to the band.

\* \* \* \* \*